United States Patent [19]
Samiotes

[11] Patent Number: 6,125,844
[45] Date of Patent: Oct. 3, 2000

[54] PORTABLE OXYGEN BASED DRUG DELIVERY SYSTEM

[75] Inventor: Nicholas G. Samiotes, Westwood, Mass.

[73] Assignee: Westwood Biomedical, Westwood, Mass.

[21] Appl. No.: 09/071,354

[22] Filed: Apr. 30, 1998

[51] Int. Cl.$^7$ .................................................. A61M 11/00
[52] U.S. Cl. ................................ 128/200.23; 128/200.12
[58] Field of Search ........................ 128/200.12, 200.14, 128/200.23, 200.21, 203.12, 203.14, 203.15, 203.21, 205.21, 200.22

[56] References Cited

U.S. PATENT DOCUMENTS

| | | | |
|---|---|---|---|
| 3,001,524 | 9/1961 | Maison | 128/200.23 |
| 3,045,671 | 7/1962 | Updegraff | 128/205.21 |
| 3,106,918 | 10/1963 | Kohl | 128/205.21 |
| 3,326,231 | 6/1967 | Hogg | 128/205.21 |
| 4,114,615 | 9/1978 | Wetterlin | 128/200.21 |
| 4,648,393 | 3/1987 | Landis et al. | 128/200.23 |
| 5,069,204 | 12/1991 | Smith et al. | 128/203.12 |
| 5,347,998 | 9/1994 | Hodson | 128/200.23 |
| 5,511,540 | 4/1996 | Bryant et al. | 128/200.23 |
| 5,875,776 | 3/1999 | Vaghefi | 128/203.15 |

*Primary Examiner*—Aaron J. Lewis
*Assistant Examiner*—Teena Mitchell
*Attorney, Agent, or Firm*—Hayes, Soloway, Hennessey, Grossman & Hage, P.C.

[57] ABSTRACT

Apparatus for portable gas-assisted dispensing of medication not using a fluorocarbon propellant. The apparatus comprises a pressurized supply of gas containing therapeutic gas or mixture of therapeutic gases, and one or more drugs mixed therein, connected to a pressure regulator, wherein the pressure regulator is connected to a gas release switch which is connected to a breath activator. The breath activator is connected to an aspiration chamber, whereby in use when a patient inhales from the aspiration chamber, the inhalation causes the breath activator to engage with the gas release switch to release the therapeutic gas/drug mixture into the aspiration chamber, wherein the therapeutic gas and drug in the aspiration chamber are simultaneously delivered to a patient during inhalation. Alternatively, medication can be stored in a separate drug reservoir adjacent the pressurized supply of therapeutic gas, which medication is drawn into the aspiration chamber by a venturi assembly. In addition, the breath activator can respond to exhalation to measure and record exhalation flow rate.

15 Claims, 10 Drawing Sheets

PORTABLE OXYGEN BASED DRUG DELIVERY SYSTEM

BACKGROUND OF THE INVENTION

1. Field of the Invention

The present invention relates to a portable or hand-held gas (oxygen) or dual therapy device comprising an inhaler for delivering oxygen or oxygen and medicine to a patient, wherein the oxygen or other gas of medicinal value serves in combined role as a propellant and therapeutic agent.

2. Prior Art

The prior art is replete with a number of disclosures that report on drug administration to a patient by using a device that atomizes the drug, wherein the patient inhales via a mouthpiece, mask or hood. For example, "inhalers" and the like are disclosed in the following U.S. Pat. No. 3,658,059 (Steil), Apr. 25, 1972; U.S. Pat. No. 4,007,238 (Glenn), Feb. 8, 1977; U.S. Pat. No. 4,116,387 (Kremer) Sep. 26, 1978; U.S. Pat. No. 4,674.491 (Brugger) Jun. 23, 1987; U.S. Pat. No. 4,746,067 (Svoboda) May 24, 1988; and U.S. Pat. No. 5,318,015 (Mansson et al.) Jun. 7, 1994.

From the above, it has now been fairly well-established that for an inhaler to be usable and effective for a wide variety of applications, patients and/or locations, it should ideally have the following characteristics: 1. the degree of atomization should be high; 2. the medicine that is stored in the device should never come in contact with surrounding air (or such contact should be kept at a minimum); 3. the medicine should be deliverable in both liquid and powder form; 4. the device should protect the patient from an overdose; 5. atomized medicine that remains in the mouthpiece, or which is still trapped, should not be wasted; 6. the inhaler should be modifiable for different types of medicines; 7. the inhaler should not be cumbersome, and 8. it should be as quiet as possible in operation so that it does not attract attention when in use.

Other citations of interest include some more recent disclosures to what have become to be known as "metered dose inhalers". For example, in U.S. Pat. No. 5,497,765 entitled "Devices for Simultaneous Delivery of Beta-2 Agonists and Oxygen to a Patient", there is disclosed a device for simultaneous delivery of beta-2 agonists and oxygen to a patient. Specifically, it was recognized therein that oxygen and beta 2 agonists are two basic medications for treating asthma in an emergency room. However, oxygen was typically administered in continuous fashion to the patient through a mouthpiece or a face mask, while beta 2 agonists were administered in the patient's throat with a metered dose inhaler. The invention therein offered the ability to administer the beta 2 agonists and oxygen simultaneously, through a set of tubes connected and in open communication with a spacer. More specifically, the device is said to comprise a main chamber, an adapter at one end of the chamber to accommodate a metered dose inhaler, and a mask or mouthpiece detachably mounted at the other end of the main chamber. A tube of given length is connected to and in open communication with the main chamber at one end, and opened to air at the other end. A unidirectional valve is placed in the tube at a short distance from the end connected to the main chamber mounted in such a manner as to allow flow circulation within the tube exclusively towards the main chamber. An auxiliary tube is connected to and in open communication with the tube at one end, at a given distance from the unidirectional valve away from the main chamber. The other end of this auxiliary tube is devised to accommodate an oxygen source.

In U.S. Pat. No. 5,031,610 entitled "Inhalation Device", there is disclosed a device for dispensing an aerosol from an aerosol module containing aerosol under pressure wherein there is a cocking device for readying it for release of the pressurized aerosol, a sear for retaining the cocking device in non-operative position following readying and a vane operable by inhalation on the part of a user to disable the sear to thus release the cocking device to effect expulsion of aerosol from the aerosol module.

In U.S. Pat. No. 5,284,133, entitled "Inhalation Device with a Dose Timer, An Actuator Mechanism, and Patient Compliance Monitoring Means", there is disclosed an inhalation device which contains a mechanism to assure patient compliance with a drug dosage regimen. That is, the history of inhalation device use can all be recorded and analyzed at a later time by a physician or other health care professional.

In U.S. Pat. No. 4,705,034 entitled "Method and Means for Dispensing Respiratory Gases by Effecting a Known Displacement", there is disclosed a device for administering oxygen and other respirating gases to a patient. More specifically, disclosed therein is a device for administering oxygen to a patient that premeters and temporarily stores single dose quantities of respirating gas and dispenses each dose in synchronization with the patient's respiratory cycle.

In U.S. Pat. No. 5,349,947 entitled "Dry Powder Inhaler and Process that Explosively Discharges a Dose of Powder and Gas From a Soft Plastic Pillow", a powder inhaler is disclosed comprising a pillow or blister-type container of extremely thin elastic construction. The pillow is compressed between an anvil with a conical depression and a confronting conical piston. Compression between the conical pillow and the conical depression produces explosive rupture of the pillow and exit of the gas and medication at a very high speed (up to supersonic) through an orifice and to the patient.

What the above review of the prior art reveals, is that although the art has developed quite extensively with regards to various inhaler designs, there is still a need for an inhaler that remains truly portable, but which eliminates the use of fluorocarbon propellants which are known to serve absolutely no role in the therapeutic process, in favor of those gases which can contribute to overall patient therapy.

Accordingly, it is an object of the present invention to provide a portable drug delivery inhaler device, that is portable in size, and which provides a unique and highly efficient "dual therapy" release of both drugs and oxygen gas, or other gases which have medicinal value, so that the patient is uniquely and conveniently administered both a gas and a medicament that combine and contribute towards the overall curative process.

SUMMARY OF THE INVENTION

Apparatus for portable gas-assisted dispensing of medication, said apparatus not using a fluorocarbon propellant, said apparatus comprising a pressurized supply of gas containing a therapeutic gas or mixture of therapeutic gases and one or more drugs mixed therein, connected to a pressure regulator, said pressure regulator connected to a gas release switch which is connected to a breath activator, which activator is connected to an aspiration chamber, whereby in use when a patient inhales from said aspiration chamber, said inhalation causes said breath activator to engage with said gas release switch to release said therapeutic gas/drug mixture into said aspiration chamber, wherein said therapeutic gas and said drug in said aspiration chamber are simultaneously delivered to a patient during inhalation.

In alternative embodiment, the present invention also comprises an apparatus for portable gas-assisted dispensing of medication, said apparatus not using a fluorocarbon propellant, said apparatus including an upper section comprising an inhaler mouthpiece, a dose release valve and an air/therapeutic gas chamber, said chamber containing a valve connected to an activation lever, said valve controlling the release of therapeutic gas to said mouthpiece as well as containing a device for pumping air from said air/therapeutic gas chamber to said mouthpiece, said valve connected to said activation lever which lever when depressed causes said valve to release said therapeutic gas and to simultaneously convey said air to said mouthpiece, said apparatus also including a lower section containing pressurized therapeutic gas and a medication chamber containing medication connected to said dose release valve and said pressurized therapeutic gas connected to and delivering therapeutic gas to said air/therapeutic gas chamber, characterized that said apparatus, upon depression of said activation lever, provides an air/therapeutic gas/medication mixture to said mouthpiece for dispensing thereof.

Finally, in yet another alternative embodiment, the present invention comprises and apparatus for portable gas-assisted dispensing of medication, said apparatus not using a fluorocarbon propellant, said apparatus including an upper section comprising an inhaler mouthpiece, a dose release valve and an therapeutic gas chamber, said chamber containing a valve connected to an activation lever, said valve controlling the release of therapeutic gas to said mouthpiece, said valve connected to said activation lever which lever when depressed causes said valve to release said therapeutic gas to said mouthpiece, said apparatus also including a lower section containing pressurized therapeutic gas and a medication chamber containing medication connected to said dose release valve and said pressurized therapeutic gas connected to and delivering therapeutic gas to said therapeutic gas chamber, characterized that said apparatus, upon depression of said activation lever, provides an therapeutic gas/medication mixture to said mouthpiece for dispensing thereof.

DETAILED DESCRIPTION OF THE PREFERRED EMBODIMENTS

Figure 1:
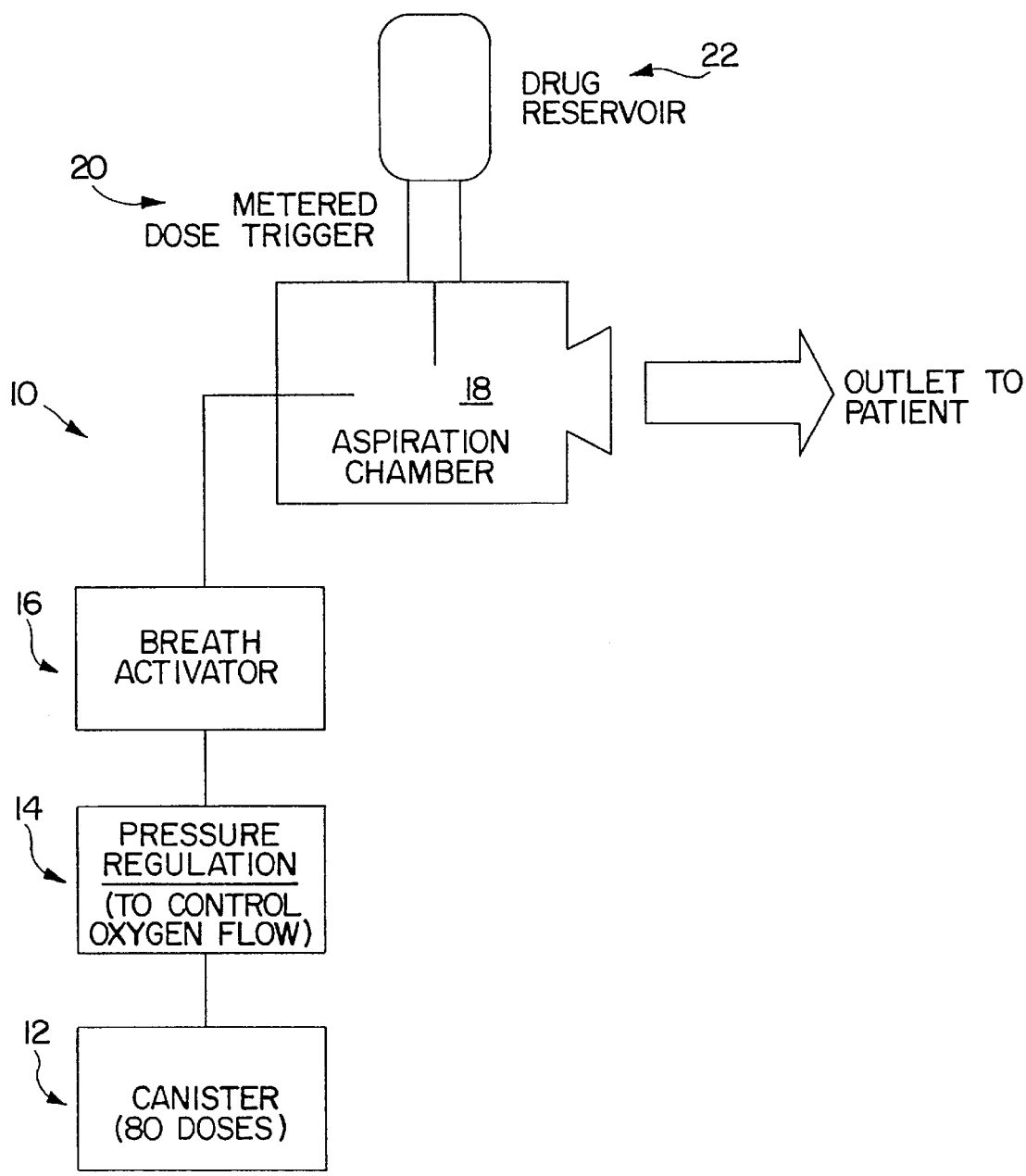
FIG. 1 is an illustration in block diagram format showing the components of one preferred apparatus of the present invention.

With reference to FIG. 1, the present invention preferably comprises an apparatus 10 for portable dispersing of medication comprising a pressurized gas supply 12 containing therapeutic gas connected to a pressure regulator 14, said pressure regulator connected to a breath activator 16 which activator is connected to an aspiration chamber 18.

In accordance with the present invention, the pressurized gas supply 12, which supplies therapeutic gas, is preferably about 2.5 inches in length and about 0.6–0.8 inches in diameter, with 0.70–0.75 inches being particularly preferred. However, other dimensions have been found suitable, such as lengths up to 3.5, 4.5 and 5.5 inches, and diameters of about 1.0 inches, or up to 1.5 inches, as the case may be. In accordance with such dimensions of the pressurized gas supply 12, the larger sizes will provide upwards of 50–100 doses, whereas the smaller sizes can provide doses below such levels, and more in the neighborhood of 10–20 doses. However, it can be appreciated that in the final analysis, dose size will be controlled by the relative concentration of therapeutic gas to non-therapeutic gas, and whether or not the device herein is vented to outside air.

The aspiration chamber 18 is further connected to a metered dose trigger 20 which trigger is connected to a drug reservoir 22 containing a drug in either liquid or powder form, whereby in use when a patient inhales from said aspiration chamber, said inhalation causes said breath activator to engage with said pressure regulator to release therapeutic gas into said aspiration chamber, said inhalation also causing said metered dose trigger to release said drug into said aspiration chamber, wherein said therapeutic gas and said drug in said aspiration chamber are mixed and simultaneously delivered to a patient during inhalation.

Figure 2:
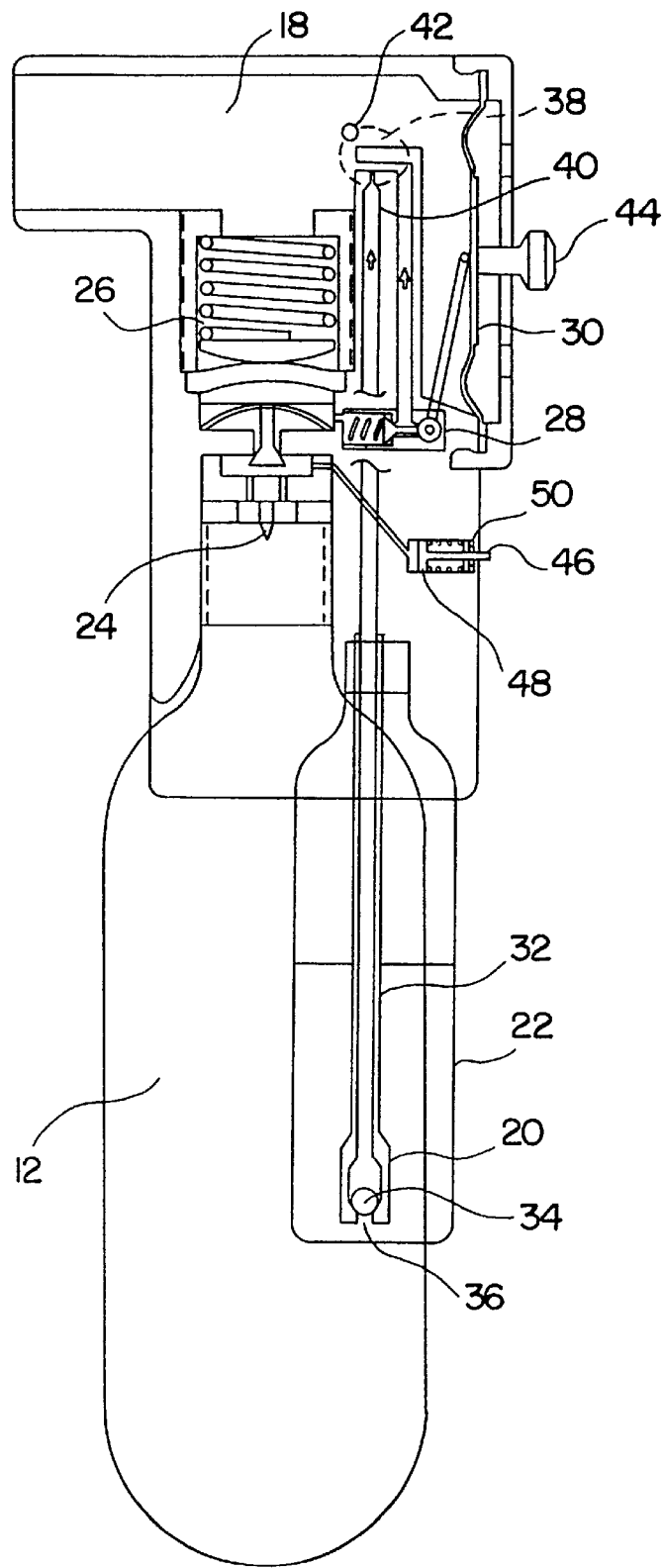
FIG. 2 is a more detailed illustration in cutaway view of the portable dispensing device of the present invention.

FIG. 2 illustrates in cutaway view the pressurized gas canister 12 containing therapeutic gas which is connected through a gas cylinder piercing assembly to the high pressure regulator 26. The pressure regulator must, in general, reduce the pressure from about 1500–3000 psi to about 25 psi. Preferably, as shown, a diaphragm and/or spring is employed. Bleed holes (not shown) can be added to assist in achieving pressure reduction. Furthermore, a baffle can be used, along with a restrictor to reduce the pressure further. Finally, an electrically pulsating valve can be employed controlled by a built-in microcomputer to electrically perform the function as shown in the preferred mechanical embodiment shown in FIG. 2.

A low pressure gas release switch is shown at 28 and a breath activator diaphragm is illustrated at 30. In operation, when the patient inhales, the breath activated diaphragm interacts with the gas release switch 28 which in communication with the pressure regulator 26 delivers therapeutic gas into the aspiration chamber 18. The gas release switch is therefore activated by the breath activator diaphragm and allows gas to exit the canister 12. As shown in the diagram, the gas release switch is conveniently a spring activated switch, however, other embodiments such as a mechanical, such as a cam, or even electrical gas valve are contemplated herein. Accordingly, the breath activator diaphragm 30, which is connected to the gas release switch 28, is designed so that upon a normal force of inhalation, said diaphragm will engage with said gas release switch 28 to release the therapeutic gas stored in canister 12.

Preferably, the breath activated diaphragm activates at a flow rate of approximately 30 liters per minute. In accordance with the present invention, a rotary or air vane could also permit that flow of therapeutic gas to occur. In addition, one could conveniently install an electrical strain gauge to the membrane as an alternative method of reducing pressure as noted above.

Also illustrated in FIG. 2 are the drug reservoir 22 and a preferred metered dose trigger mechanism 20. This preferred metered dose mechanism 20 allows a measured and metered dose of drug or other element to be added and delivered to the therapeutic gas stream as it is being inhaled. The preferred dose mechanism 20 is a check valve. A ball floats in the reservoir 22 at the bottom of thereof. As therapeutic gas flows it begins to lift up the ball until it shut down the stream of drug flow. The drug is therefore conveniently and uniquely measured by the size of the chamber 22 as well as the diameter of tube 32 and the size of the ball 34 and the opening 36.

Accordingly, drug in reservoir 22 is brought up to the atomization chamber 38 by the venturi assembly 40. An air vent for gas metering is shown at 42. Alternatively one can employ a Bernoulli channel aspirated to the user. The drug stored in reservoir 22 can be either of liquid or powder form and is therefore carried to the user along with the therapeutic gas in through the preferred venturi design.

Those skilled in the art will also recognize that the drug delivery system may take the form of a disk with individual or premeasured compartments. Such would be similarly coupled with the therapeutic gas and get carried along with same. It would then rotate to provide a fresh dose upon subsequent activation. Finally, in the context of the present invention, a non-mechanical system would operate to similarly provide controlled metering of drug delivery via a microprocessor.

Figure 5:
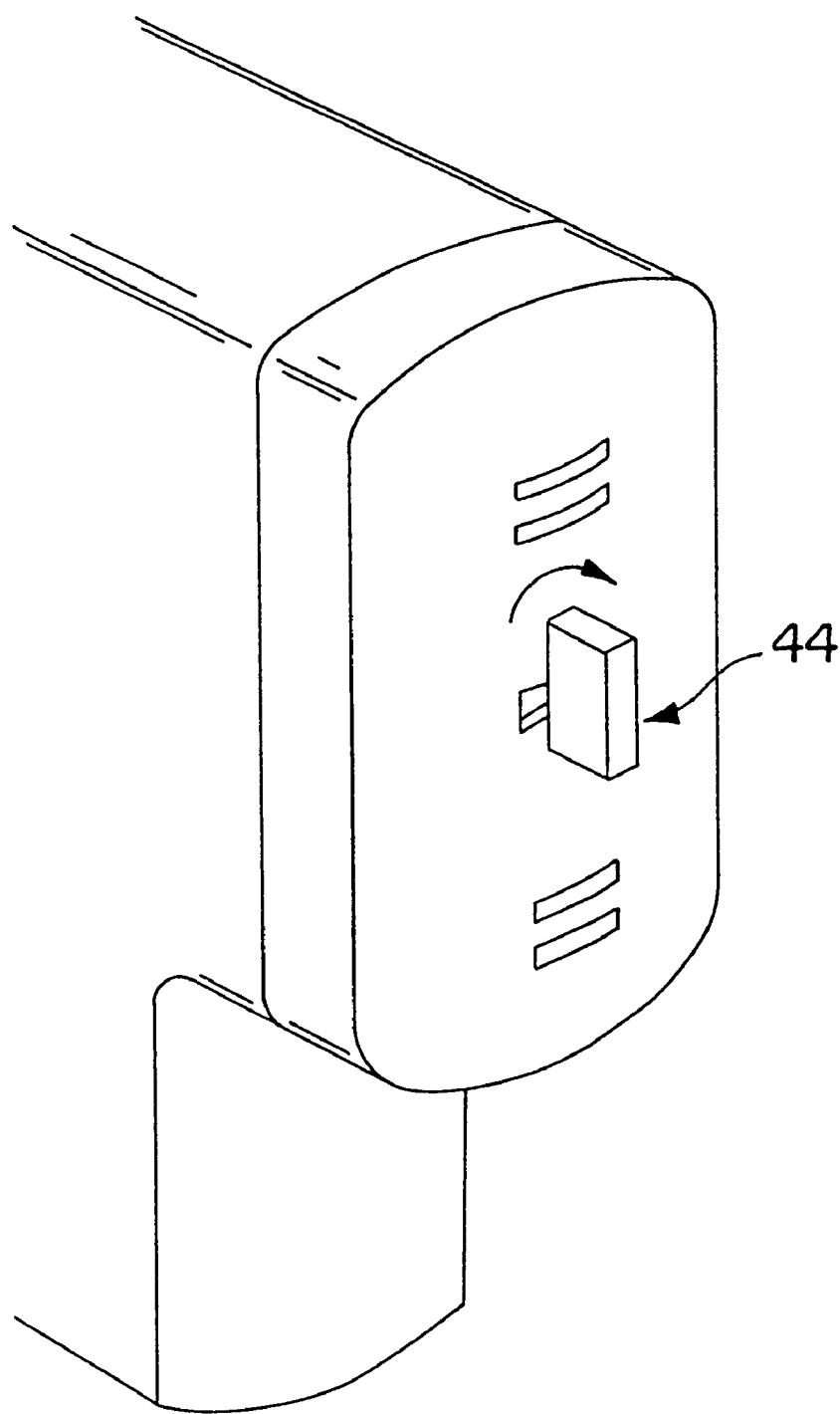
FIG. 5 is a representative view of the on/off switch of the present invention.

An on/off switch is shown at 44. The switch is attached to the breath activated diaphragm 30. Preferably, in the "off" position, it is pulled through a slot and twisted 45 degrees which prevents the diaphragm from moving. In the "on" position it is twisted another 45 degrees and freely moves in the slot which then allows the diaphragm to operate. The on/off switch of such preferred design is shown more clearly in representative view in FIG. 5. Alternatively, one could employ an electrical switch.

A low dose indicator is also preferably supplied at 46. This indicator is based on a tire pressure indicator or spool valve technology. It consists of a piston 48, O-rings and an indicator post attached to the piston. Accordingly, as the pressure in the oxygen cylinder decreases the post will pop out indicating that it is time to change the gas and medication cylinders. Preferably, the medication is over-filled so that it will not run out before the gas, or the gas will not run out before the medication.

Alternatively, the low dose indicator could be provided electrically via a strain gauge and a membrane. Furthermore, if desired, one could readily add a display coupled to the low dose indicator wherein a microprocessor would record dosages taken each day, thereby recording date and time, wherein said information could be stored in the unit over a few weeks time, or longer as may be the case. That is, the low dose indicator would monitor the doses delivered. In addition, one could then add a serial port so that such information could be readily down-loaded to a host and ultimately to the physician to monitor patient compliance. Such down-load of information could preferably be transmitted via wire attachment to said serial port, or via infrared or other wireless types of transmission.

Figure 3:
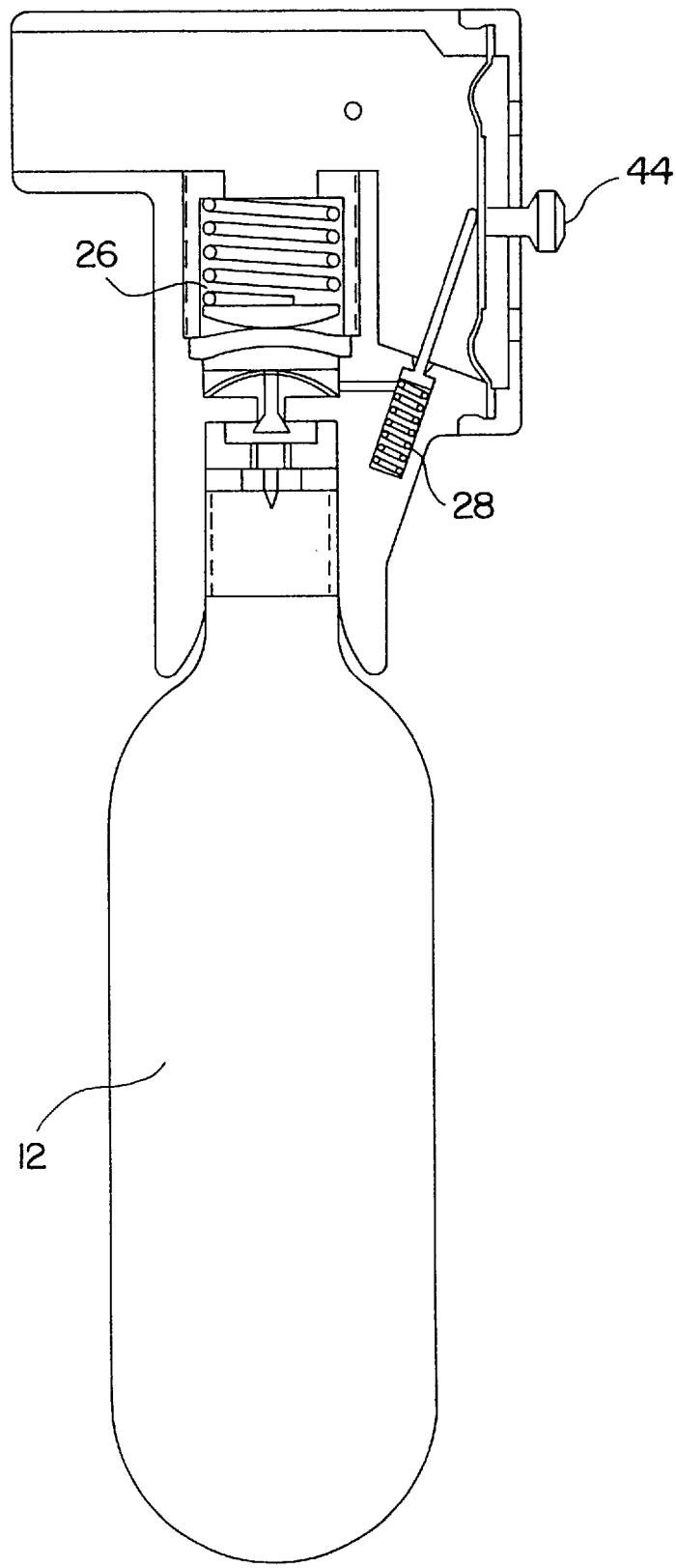
FIG. 3 is another detailed illustration in cutaway view of the portable dispensing device of the present invention wherein drug for delivery is mixed directly with the therapeutic gas propellant in the gas canister.

However, the above illustrations only depict one preferred embodiment of the present invention, and in alternative preferred embodiment, the drug reservoir 22 and metered dose trigger 20 can be completely eliminated, in favor of mixing the drug for delivery directly with the therapeutic gas propellant in the gas canister 12. This is best illustrated in FIG. 3. Other aspects of FIG. 3, similar to FIG. 2, are the pressure regulator 26 and on/off switch connected to the low pressure gas release switch 28.

In addition, and in further optional embodiment, one can add an additional spacer chamber between the outlet of the aspiration chamber and the patient. By such design, the spacer chamber allows for a cloud of mist to be formed prior to being inhaled by the patient.

Preferably, the therapeutic gas in the gas canister 12 is oxygen, specifically, medical grade oxygen, and in the broad context of the present invention, the canister 12 may contain air or other oxygen containing gas mixtures of therapeutic value. For example, other therapeutic gases include compressed air, carbon dioxide, helium, nitrogen, nitrous oxide, and nitric oxide and mixtures thereof. Furthermore, one can conveniently add to the therapeutic gases the following additives: herbs, nicotine (for the control of smoking), flavors for refreshment, pain medication, anesthetics, and respiratory drugs. In addition, in the broad context of the utility of the present invention, diabetic could use the device herein for insulation therapy via inhalation.

Figure 4:
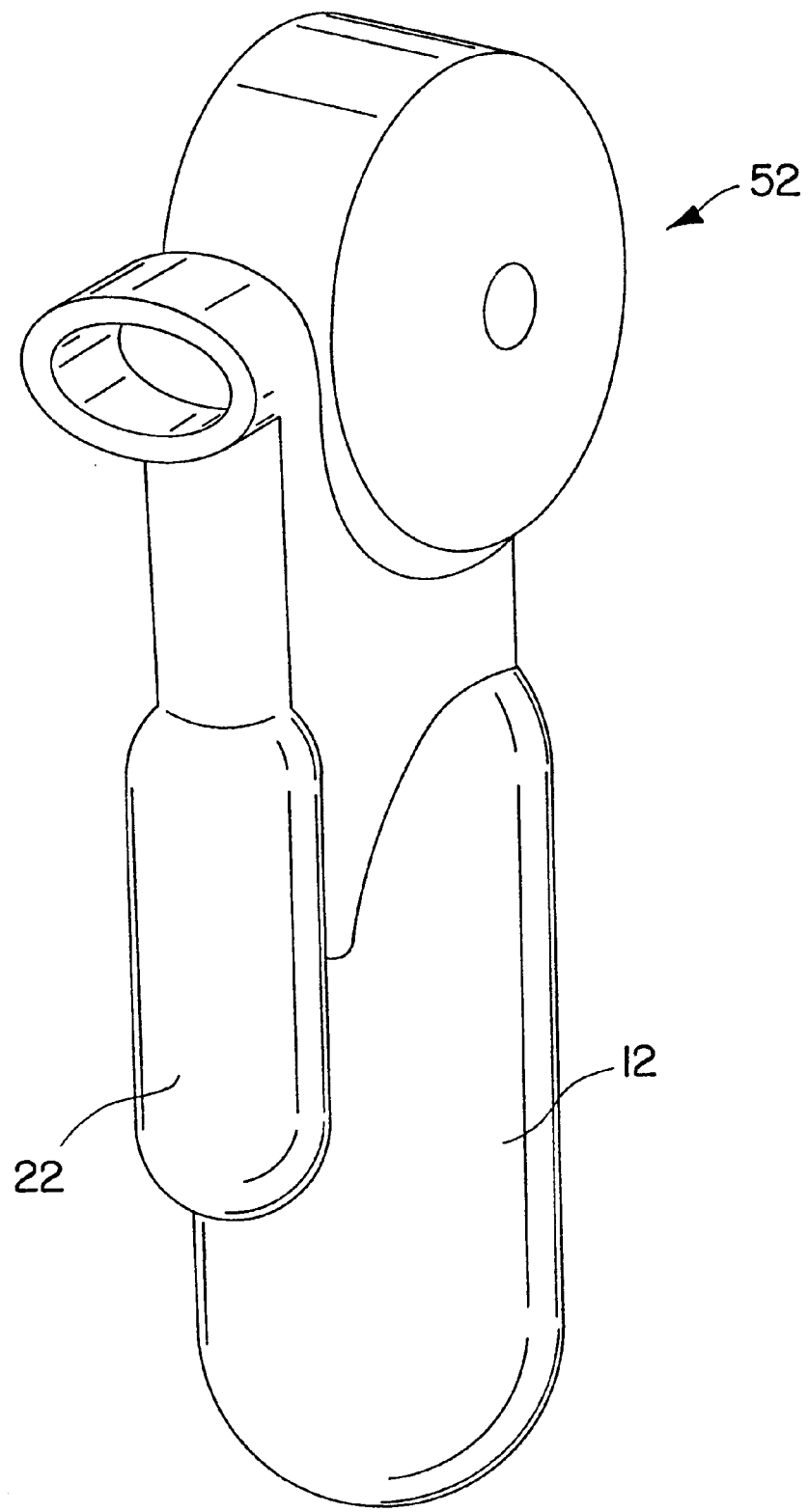
FIG. 4 is a representative view of the device of the present invention.
Figure 6:
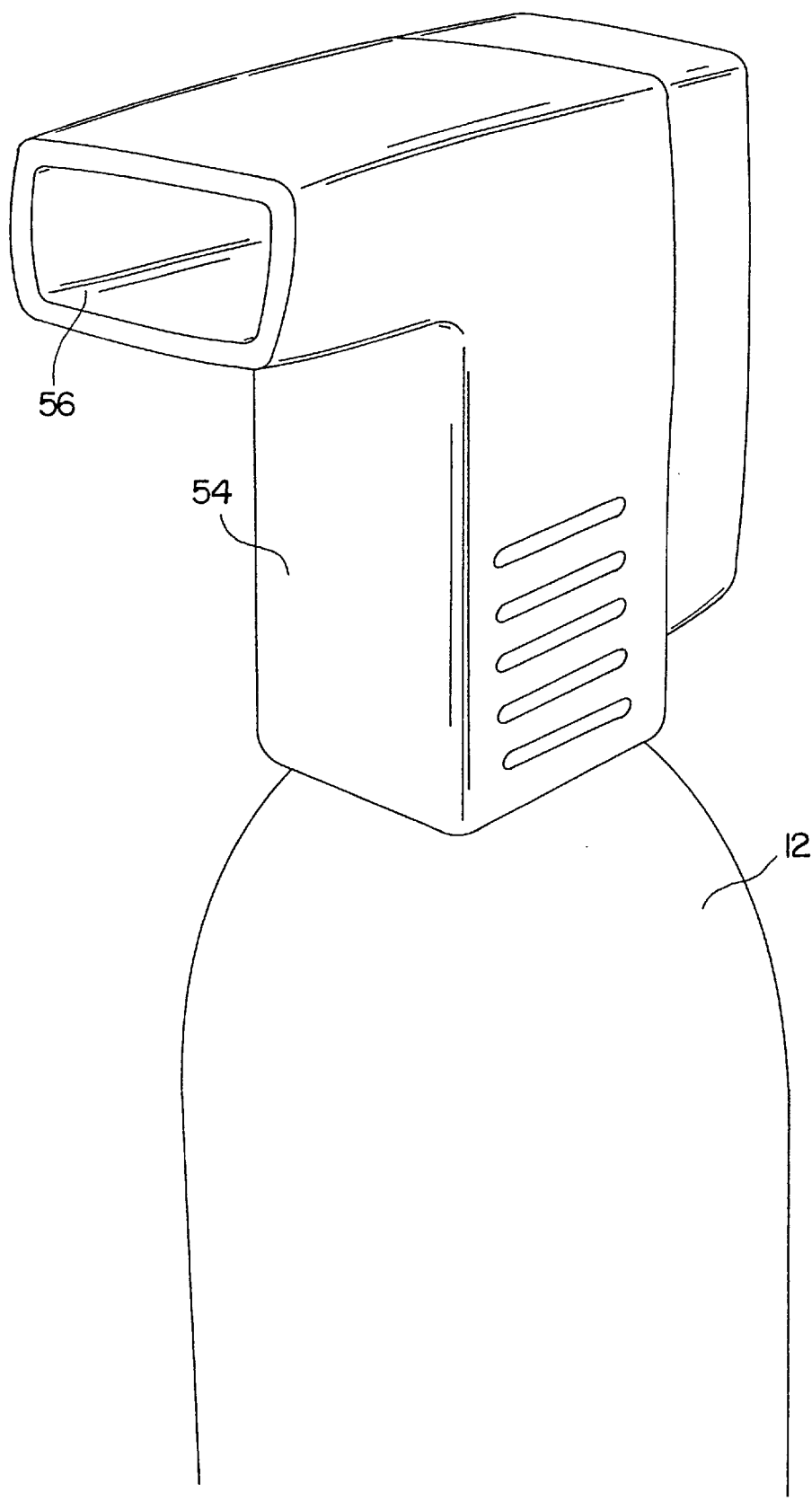
FIG. 6 is yet another representative view of the device of the present invention, in alternative geometry thereof.

Turning to FIG. 4, as shown therein in representative view, the canister 12 and drug reservoir 22 are positioned adjacent one another to improve the portable aspects of the present invention, and the top of the unit containing the high pressure regulator, low pressure gas release switch, etc., can be conveniently housed into an assembly housing 52 that itself is preferably about 1.0 inch in diameter and 1.0 inch in length and preferably screws on top of the canister 12. In addition, in the act of screwing the housing 52 on the canister 12, one can conveniently pierce the canister top by the gas cylinder piercing assembly 24. Furthermore, as shown in representative view in FIG. 6, the device of FIG. 3 can be conveniently housed in housing 54 and attached to canister 12 which contains both therapeutic gas and drug to be delivered at 56 upon inhalation thereof.

Attention next is directed to FIG. 7, which illustrates another alternative embodiment of the present invention in what is a closed position, as to be described more fully below. At 58 can be seen the medication capsule and oxygen case. That is, 58 contains preferably an oxygen canister 60 (or other therapeutic gas) and medication 62 therein. Furthermore, at 64 is the oxy-haler module, which module contains dose release valve 66, atomizer tube 68 and activation lever 70. In addition, at 72 is an oxygen valve and air pump, and at 74 and 76 are an air chamber, and oxygen chamber, respectively. The inhaler mouthpiece is shown at 78.

As noted above, FIG. 7 represents a view in closed position, and as can now be appreciated upon view of FIG. 7, in such position, the oxygen, medication and air chambers are full and the oxygen and dose release valves, 66 and 72 respectively, are both closed. Accordingly, there is no flow and no leakage.

Figure 8:
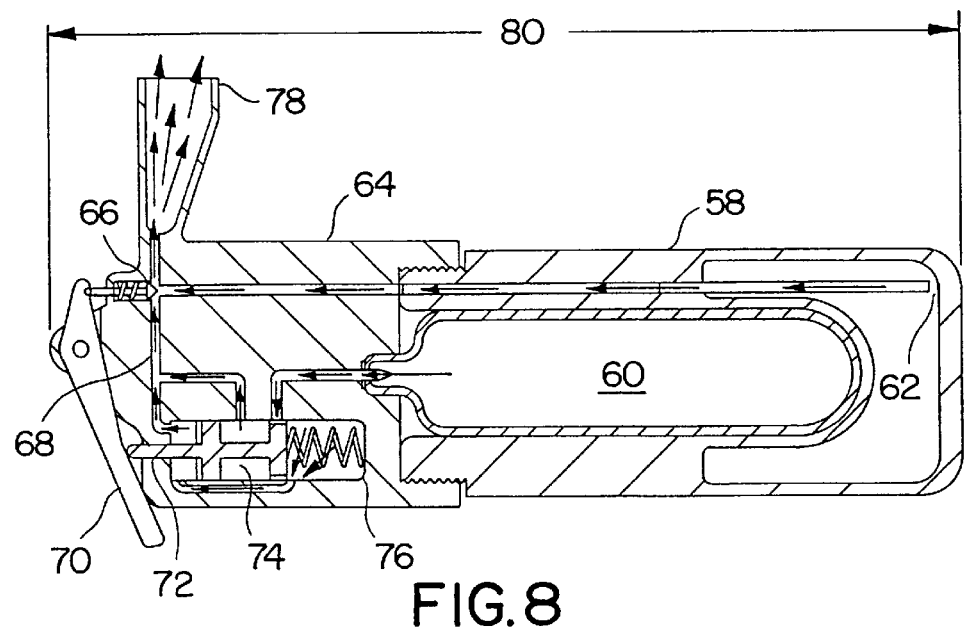
FIG. 8 is similar to FIG. 7, illustrating the embodiment therein in open position.

Attention is directed to FIG. 8 which illustrates the open position thereof. The arrows therein in indicate general flow pathways. Accordingly, as the activation lever 70 is depressed the dose release valve 66 will open and oxygen 60 will begin to flow. The air pump 72 will also inject a blast of air into the atomizer tube and mix with the oxygen to insure good atomization. As the air/oxygen mixture passes through the tube the medication will be picked up and will exit as a mixture of air/oxygen and medication. When the activation lever 70 is released the air and oxygen chamber will refill and be ready for the next dose. The dose release valve 66 will also close to prevent any leakage of medication. Pressure regulation will be accomplished as shown by the number of tube orifices and baffles (not shown). Finally, it is noted that the size of the apparatus, shown at 80, is about 5.5 inches (12.7 cm), and the unit can be one integral piece, and is totally disposable. Alternatively, 64 or 58 can be manufactured independently, joined together, e.g., by screwing 58 into 64, or vice versa, and can be separately disposed, or separately reused.

Figure 7:
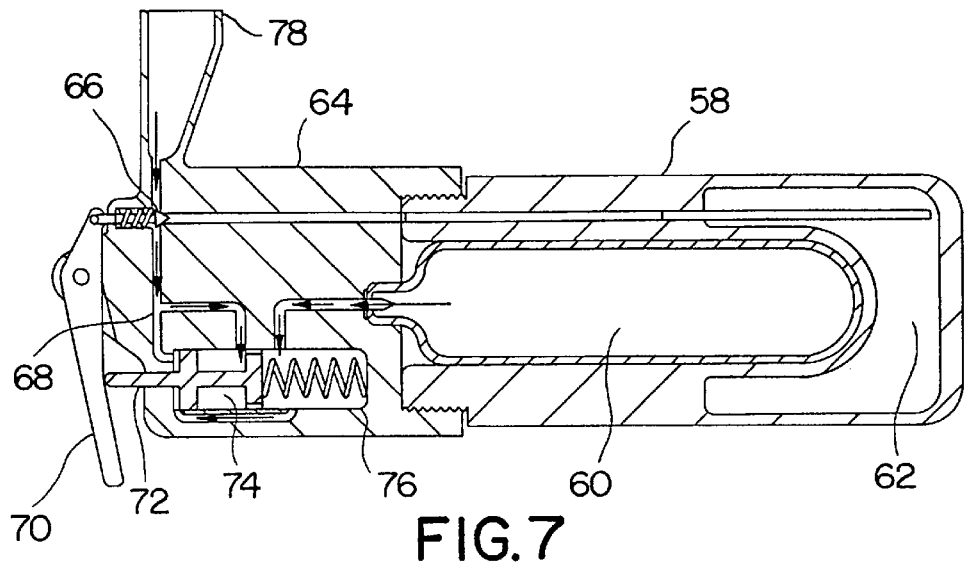
FIG. 7 is another detailed illustration in cutaway view of another preferred embodiment of the portable dispensing device of the present invention, in a closed position.

In addition, breath activation can be accomplished in the embodiments of FIGS. 7 and 8 in the same manner as illustrated in FIG. 2, however, wherein the dose release valve 66 and air/oxygen flow will be controlled by the breath activated mechanism. That is, the activation lever 70 is replaced by the breath activation mechanism (see items 26, 28, and 30 of FIG. 2).

Figure 9:
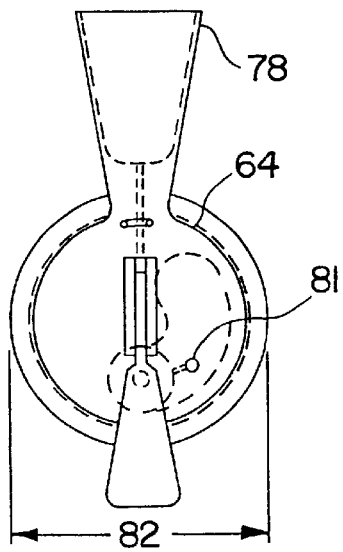
FIG. 9 is a top view of the embodiment of FIGS. 7 and 8.

FIG. 9 is a top view of the embodiment of FIGS. 7 and 8. At 78 is again the inhaler mouthpiece and the top of the oxy-haler module is seen again at 64. An empty indicator is illustrated at 81. The diameter 82 is preferably about 1.5 inches (3.81 cm).

Accordingly, in this alternative embodiment shown in FIGS. 7 and 8, the device has both an air chamber and an oxygen chamber the size of which allows the venturi to draw from the medication reservoir, and will draw only when the oxygen is allowed to flow and the air pump pumps. In this embodiment the air is then an assist and is present since the compressed gas pressure will change as the gas is depleted.

Finally, before leaving the discussion of the embodiment illustrated in FIGS. 7 and 8, as can be seen therein, the upper section is illustrated as the oxy-inhaler module 64, and the lower section 58 contains the medication capsule 62 and oxygen (or therapeutic gas) case. Accordingly, the apparatus may be manufactured as one continuous piece, or, in alternative embodiment, the upper section and said lower sections can be separated from one another for convenient disposal.

Figure 10:
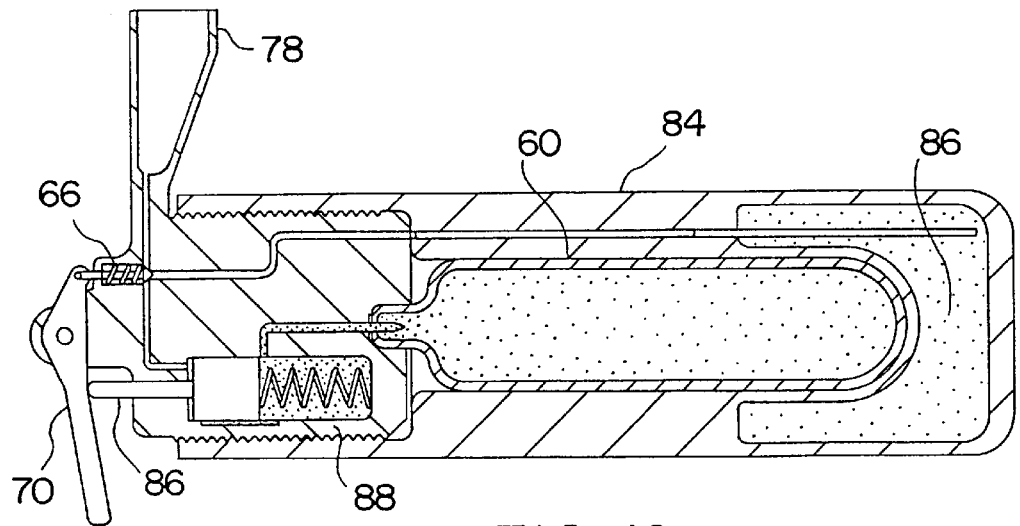
FIGS. 10 and 11 are similar to the embodiments of FIGS. 7 and 8, wherein the air chamber has been eliminated.
Figure 11:
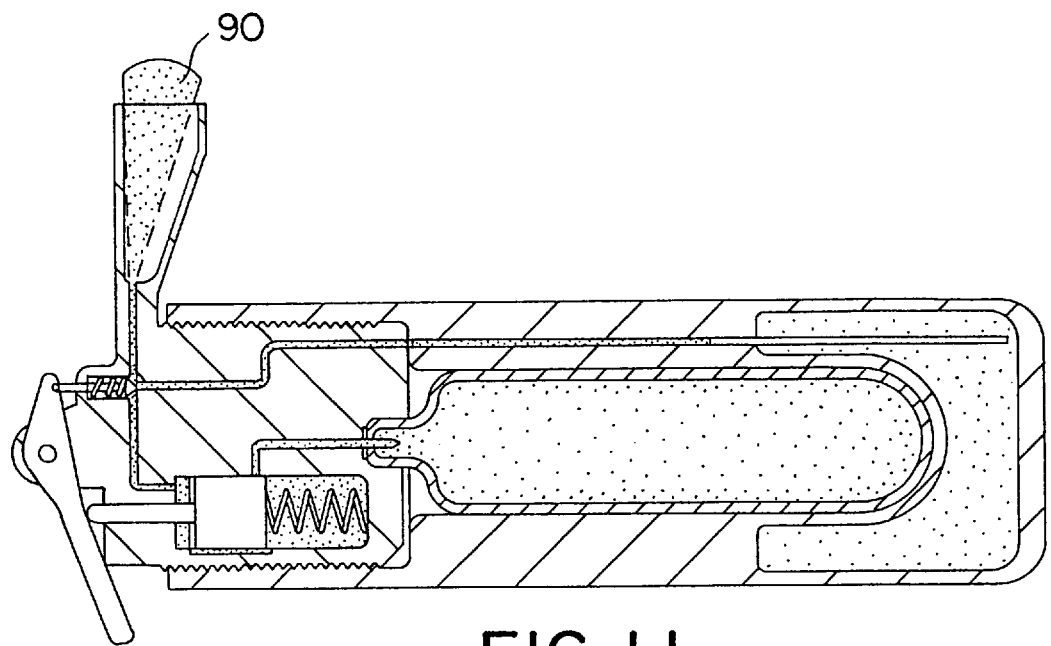

A modification of the embodiments shown in FIGS. 7 and 8 is illustrated in FIGS. 10 and 11, which is similar, except that the air chamber 74 has been eliminated. With reference to FIG. 10, which is again the closed position, the medication case is shown at 84 containing medication 86 and oxygen capsule 88. An inhaler mouthpiece is again shown as item 78 as well as activation lever, along with dose release valve 66. The oxygen release valve is illustrated at 86, as well as oxygen chamber. Accordingly, when the activation lever is depressed, and the oxygen release valve is moved downwardly (FIG. 11) the apparatus is placed in the open position and oxygen along with medication exits at 90.

Finally, before discussing the utility of the present invention, it is worth pointing out some further alternative modifications to the invention herein. For example, chief among these alternative is the addition of a mechanical or electrical timer that prevents overuse of the device, which timer would be conveniently installed to prevent activation of the breath activated assembly 30. That is, such mechanical device mechanism would work in opposite direction and force to the breath activated assembly 30 to prevent delivery of therapeutic gas and or desired drug. Accordingly, the patient can be conveniently regulated and prevented from over-dosing, in those cases where drugs of an addictive nature are involved.

Figure 12:
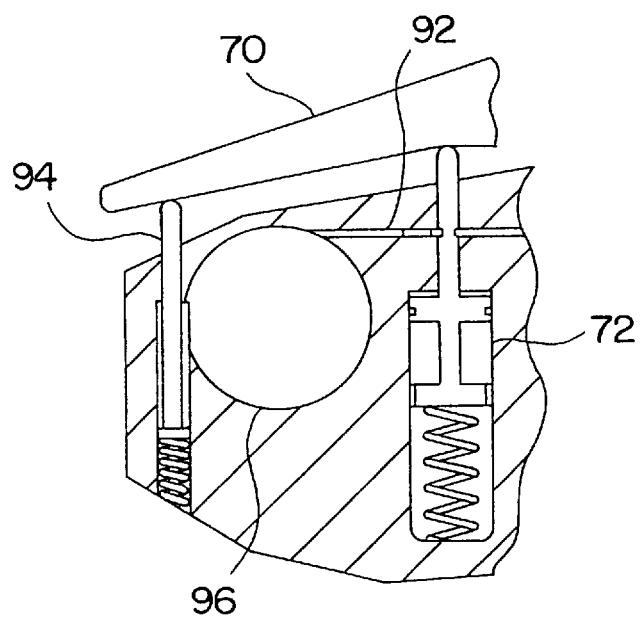
FIG. 12 illustrates the mechanical time delay mechanism for regulating the release of the therapeutic gas/drug mixture over a selected period of time.

An illustration of the mechanical time delay mechanism is seen in FIG. 12. As seen therein, activation lever 70 is again in communication with oxygen valve and air pump 72 within the oxy-haler module 64. In addition, a stop latch 92 is incorporated therein along with a timer rod and time delay device 96. Accordingly, when the oxy-haler is in the ready mode and the medication release lever is depressed, the medication will be delivered and the time rod will move down into the cocked position. When the lever is released, the timer rod will return to the up position and this action will position the stop latch so as to prevent the oxygen valve from operating and will also allow the timer rod to move up by the spring. This in turn will coil the negator spring which will set the delay timer to its designed time, e.g., 5 minutes. When the time delay has elapsed, the timer device will release the latch and allow the medication lever to be activated.

The time delay device 96 is preferably either an analog or digital design. The analog design comprises a resistor and capacitor attached to a timer chip. The digital design preferably includes a counter or processor with a timer function controlled by standard software.

In addition, it is worth noting that with respect to an inhaler device, it is very important to have a certain geometry to the spray, which is known as the plume geometry in the metered dose inhaler industry. Since the device herein preferably uses oxygen or compressed gas, such gas may be conveniently relied upon to alter and/or shape the inhaled spray.

Figure 13:
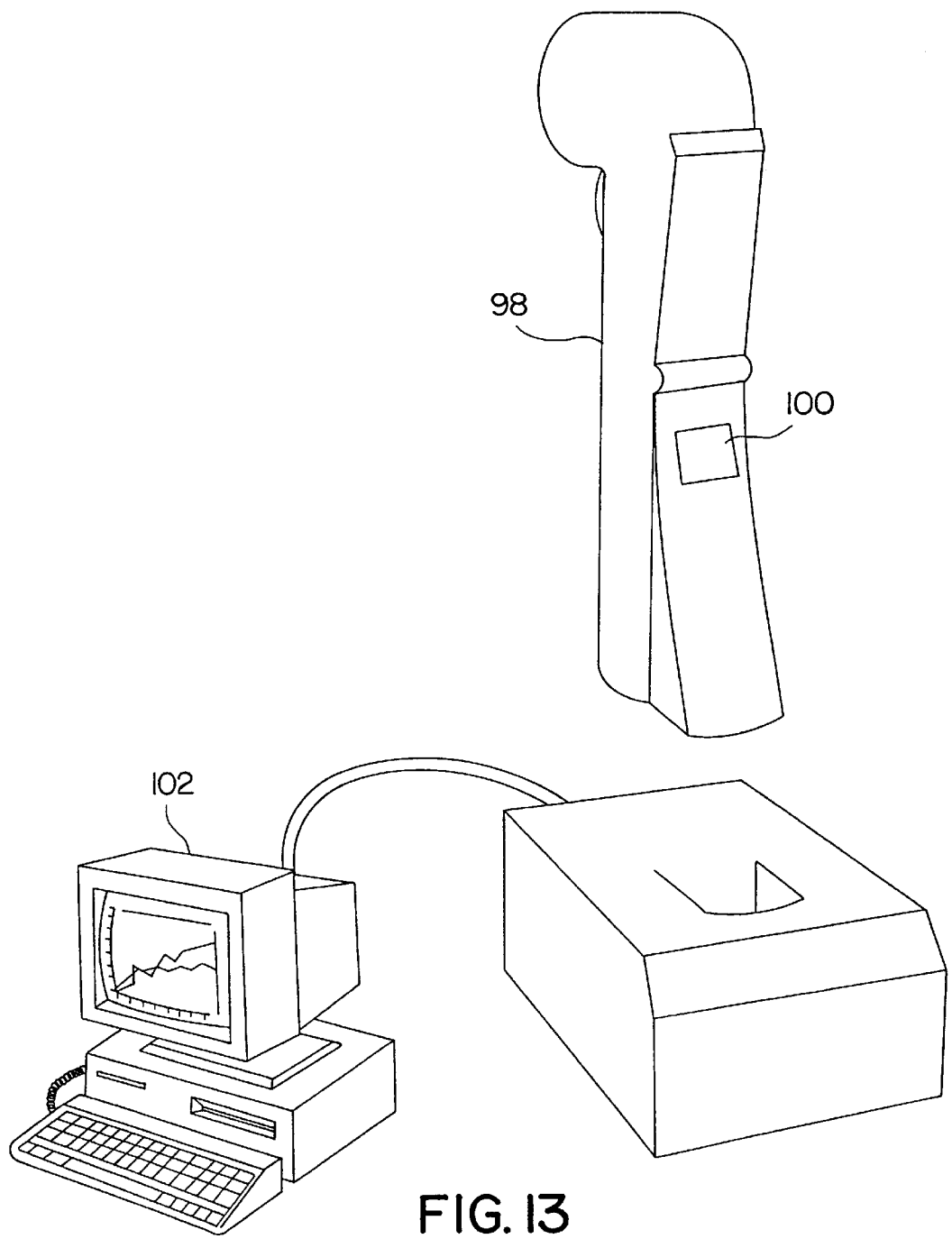
FIG. 13 illustrates a preferred embodiment of the present invention, wherein the portable gas assisted device for dispensing of medication is shown in product form with the associated electronic tracking capability.

Finally, attention is directed at FIG. 13, which, as previously noted, illustrates the preferred embodiment of the present invention wherein the apparatus for portable dispensing of therapeutic gas/medication is shown in one preferred product form. That is, at 98 is the apparatus which houses the previously mentioned pressurized gas supply 12 for supply of therapeutic gas, as well as drug reservoir 22. Of course, optionally, 98 could contain therapeutic gas mixed with drug or medication as illustrated in FIG. 3. In addition, apparatus 98 is made to contain the low dose indicator which is coupled to the aforementioned microprocessor, as well as to display 100. In addition, apparatus 98 is also made to provide "peak-flow" monitoring, which refers to the so-called "peak-flow" indication that an asthmatic patient provides upon exhale thereof. In other words, breath activation diaphragm is connected to an appropriate strain gauge which connected to the microprocessor will record the peak flow of the patient upon exhalation. Accordingly, peak-flow data, as well as a record of the number of doses delivered to the patient, can then be downloaded to a computer host tracking system shown generally at 102.

In the context of the utility of the present invention, a variety of utilities are contemplated. For example, by virtue of the present invention, the use of oxygen and/or mixtures of other gases as the propellant provides the patient with a dual therapy of both drug and oxygen, or other therapeutic gases, thereby assisting them in controlling their particular disease. For example, in the cases of asthmatic patients, such patients would not only receive the necessary medication, such patients would also be provided with controlled doses of oxygen, thereby more effectively providing relief, and improving the overall drug delivery protocol as compared to current metered dose inhalers or dry powdered inhalers.

In addition, it should be recognized herein that the device of the present invention will play a leading role in pain management, by making the delivery of pain management drugs such as nitrous oxide more readily available. In effect, the device herein creates for the first time the opportunity for production of a portable patient controlled inhaled analgesic system which will allow patients to conveniently control pain therapy within prescribed limits.

Other embodiments of and uses for this invention will be apparent to those skilled in the art without departing form the spirit and scope of the following claims.

I claim:

1. Apparatus for portable gas-assisted dispensing of medication, said apparatus employing a fluorocarbon-free compressed gas propellant, said apparatus including an upper section comprising an inhaler mouthpiece, a dose release valve and an air/therapeutic gas chamber, said chamber containing a valve connected to an activation lever, said valve controlling the release of therapeutic gas to said mouthpiece as well as containing a device for pumping air from said air/therapeutic gas chamber to said mouthpiece, said valve connected to said activation lever which lever when depressed causes said valve to release said therapeutic gas and to simultaneously convey said air to said mouthpiece, said apparatus also including a lower section containing a pressurized therapeutic gas selected from the group consisting of oxygen, air, carbon dioxide, nitrous oxide, nitrogen, nitric oxide, helium and a mixture thereof, and a medication chamber containing medication connected to said dose release valve and said pressurized therapeutic gas connected to and delivering therapeutic gas to said air/therapeutic gas chamber, wherein said apparatus, upon depression of said activation lever, provides an air/therapeutic gas/medication mixture to said mouthpiece for dispensing thereof.

2. The apparatus of claim 1, wherein said upper section includes an atomizer tube connected to said air/therapeutic gas chamber which atomizer tube atomizes said air/therapeutic gas/medication mixture prior to release in said mouthpiece.

3. The apparatus of claim 1, further including a timer mechanism which mechanism controls said activation lever from engaging with said valve to thereby regulate the release of said air/therapeutic gas/medication mixture over a selected period of time.

4. The apparatus of claim 1 wherein said upper section and said lower sections can be separated from one another for reuse or disposal.

5. Apparatus for portable gas-assisted dispensing of medication, said apparatus employing a fluorocarbon-free compressed gas propellant, said apparatus including an upper section comprising an inhaler mouthpiece, a dose release valve and an air/therapeutic gas chamber, said chamber containing a valve connected to breath activator, said valve controlling the release of therapeutic gas to said mouthpiece as well as containing a device for pumping air from said air/therapeutic gas chamber to said mouthpiece, said valve connected to said breath activator which activated by inhalation at said inhaler mouthpiece causes said valve to release said therapeutic gas and to simultaneously convey said air to said mouthpiece, said apparatus also including a lower section containing a pressurized therapeutic gas selected from the group consisting of oxygen, air, carbon dioxide, nitrous oxide, nitrogen, nitric oxide, helium and a mixture thereof, and a medication chamber containing medication connected to said dose release valve and said pressurized therapeutic gas connected to and delivering therapeutic gas to said air/therapeutic gas chamber, wherein said apparatus, upon activation of said breath activator delivers an air/therapeutic gas/medication mixture to said mouthpiece for dispensing thereof.

6. The apparatus of claim 5, wherein said upper section includes an atomizer tube connected to said air/therapeutic gas chamber which atomizer tube atomizes said air/therapeutic gas/medication mixture prior to release in said mouthpiece.

7. The apparatus of claim 5, further including a timer mechanism which mechanism controls said breath activator from engaging with said valve to thereby regulate the release of said air/therapeutic gas/medication mixture over a selected period of time.

8. The apparatus of claim 5 wherein said upper section and said lower sections can be separated from one another for reuse or disposal.

9. Apparatus for portable gas-assisted dispensing of medication, said apparatus employing a fluorocarbon-free pressurized gas propellant, said apparatus including an upper section comprising an inhaler mouthpiece, a dose release valve and a therapeutic gas chamber, said chamber containing a valve connected to an activation lever, said valve controlling the release of therapeutic gas to said mouthpiece, said valve connected to said activation lever which lever when depressed causes said valve to release said therapeutic gas to said mouthpiece, said apparatus also including a lower section containing a pressurized therapeutic gas selected from the group consisting of oxygen, air, carbon dioxide, nitrous oxide, nitrogen, nitric oxide, helium and a mixture thereof and a medication chamber containing medication connected to said dose release valve and said pressurized therapeutic gas connected to and delivering therapeutic gas to said therapeutic gas chamber, wherein said apparatus, upon depression of said activation lever, provides a therapeutic gas/medication mixture to said mouthpiece for dispensing thereof.

10. The apparatus of claim 9, wherein said upper section includes an atomizer tube connected to said air/therapeutic gas chamber which atomizer tube atomizes said air/therapeutic gas/medication mixture prior to release in said mouthpiece.

11. The apparatus of claim 9, further including a timer mechanism which mechanism controls said breath activator from engaging with said valve to thereby regulate the release of said air/therapeutic gas/medication mixture over a selected period of time.

12. The apparatus of claim 9 wherein said upper section and said lower sections can be separated from one another for reuse or disposal.

13. Apparatus for portable gas-assisted dispensing of medication, said apparatus employing a fluorocarbon-free pressurized gas propellant, said apparatus including an upper section comprising an inhaler mouthpiece, a dose release valve and an air/therapeutic gas chamber, said air/therapeutic gas chamber containing a valve connected to breath activator, said valve controlling the release of therapeutic gas to said mouthpiece, said valve connected to said breath activator which when activated by inhalation at said inhaler mouthpiece causes said valve to release said therapeutic gas to said mouthpiece, said apparatus also including a lower section containing a pressurized therapeutic gas selected from the group consisting of oxygen, air, carbon dioxide, nitrous oxide, nitrogen, nitric oxide, helium and a mixture thereof, and a medication chamber containing medication connected to said dose release valve, and said pressurized therapeutic gas connected to and delivering therapeutic gas to said air/therapeutic gas chamber, wherein said apparatus, upon activation of said breath activator delivers an air/therapeutic gas/medication dose mixture to said mouthpiece for dispensing thereof.

14. The apparatus of claim 13, further including a low dose indicator which indicator measures and records the number of said air/therapeutic gas/medication dose mixtures dispensed.

15. The apparatus of claim 14 wherein said breath activator is connected to a strain gauge wherein said breath activator further responds to exhalation flow and said strain gauge measures said exhalation flow.

* * * * *